(12) United States Patent
Corndorf

(10) Patent No.: US 9,008,789 B2
(45) Date of Patent: *Apr. 14, 2015

(54) SYSTEM AND METHOD FOR SMOOTHING SAMPLED DIGITAL SIGNALS

(75) Inventor: Eric D. Corndorf, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/567,188

(22) Filed: Aug. 6, 2012

(65) Prior Publication Data

US 2012/0303329 A1  Nov. 29, 2012

Related U.S. Application Data

(63) Continuation of application No. 11/691,115, filed on Mar. 26, 2007, now Pat. No. 8,315,709.

(51) Int. Cl.
| | |
|---|---|
| *A61N 1/00* | (2006.01) |
| *A61N 1/37* | (2006.01) |
| *A61N 1/02* | (2006.01) |
| *H03M 7/40* | (2006.01) |
| *A61B 5/00* | (2006.01) |

(52) U.S. Cl.
CPC ............ *A61N 1/3702* (2013.01); *A61B 5/0006* (2013.01); *A61B 5/0031* (2013.01); *A61N 1/025* (2013.01); *H03M 7/40* (2013.01); *A61B 5/7239* (2013.01); *A61B 5/7232* (2013.01)

(58) Field of Classification Search
USPC ................ 607/2, 6, 60; 600/323, 508–509, 600/515–519; 386/114; 341/67, 106–107, 341/155

See application file for complete search history.

(56) References Cited

U.S. PATENT DOCUMENTS

| | | | |
|---|---|---|---|
| 4,449,536 A | 5/1984 | Weaver | |
| 5,139,028 A | 8/1992 | Steinhaus et al. | |
| 5,379,757 A | 1/1995 | Hiyama et al. | |
| 5,549,649 A * | 8/1996 | Florio et al. | ............. 607/15 |
| 5,623,935 A | 4/1997 | Faisandier | |
| 5,722,999 A | 3/1998 | Snell | |
| 5,782,885 A * | 7/1998 | Andersson | ............. 607/17 |
| 6,466,625 B1 | 10/2002 | Kobayashi et al. | |
| 6,470,065 B1 | 10/2002 | Lauther | |
| 6,697,672 B2 * | 2/2004 | Andersson | ............. 607/17 |
| 7,315,815 B1 | 1/2008 | Gersho et al. | |
| 7,766,830 B2 | 8/2010 | Fox et al. | |
| 2002/0193668 A1 | 12/2002 | Munneke et al. | |
| 2003/0083581 A1 | 5/2003 | Taha et al. | |
| 2004/0015081 A1 | 1/2004 | Kramer et al. | |
| 2004/0158295 A1 * | 8/2004 | Dyjach et al. | ............. 607/25 |
| 2006/0051068 A1 | 3/2006 | Gomila | |

(Continued)

OTHER PUBLICATIONS

Cox et al., "Compact Digital Coding of Elctrocardiographic Data," Abstract, Washington University, St. Louis, Missouri. et al, 1972.

(Continued)

*Primary Examiner* — Rex R Holmes
(74) *Attorney, Agent, or Firm* — Evans M. Mburu

(57) ABSTRACT

Waveforms are digitally sampled and compressed for storage in memory. The compression of the data includes generating a truncated entropy encoding map and using the values within the map to obtain good compression. An encoder further sub-selects values to be encoded and values to remain unencoded to provide an overall compression of the data.

3 Claims, 16 Drawing Sheets

(56) References Cited

U.S. PATENT DOCUMENTS

2006/0094968 A1    5/2006  Drew
2007/0016095 A1*   1/2007  Low et al. .................... 600/544
2007/0123758 A1*   5/2007  Miesel et al. ................ 600/301

OTHER PUBLICATIONS

Horspool et al., "An LZ Approach to ECG Compression," Abstract, IEEE Symposium on Computer-Based Medical Systems, Jun. 1994, pp. 71-76.

Pahlm et al., "Compact Digital Storage of ECGs," Computer Programs in Biomedicine, vol. 9, 1979, pp. 293-300.

Jalaleddine et al., "ECG Data Compression Techniques—A Unified Approach," IEEE Transactions on Biomedical Engineering, vol. 37, No. 4, Apr. 1990, pp. 329-343.

Brito et al, A Predictive Adaptive Aproach to Generic ECG Data Compression, Intelligent Signal Processing, 2005 IEEE International Workshop on Sep. 1, 2005 pp. 32-37.

International Search Report, PCT/US2008/057414, May 8, 2008, 6 Pages.

* cited by examiner

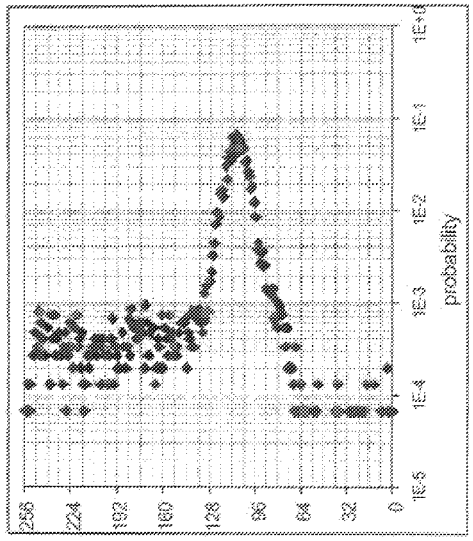
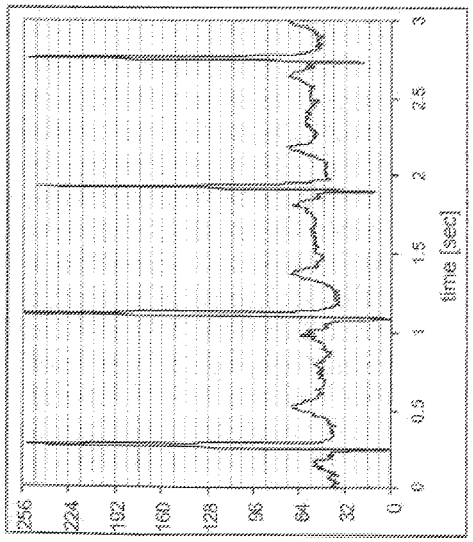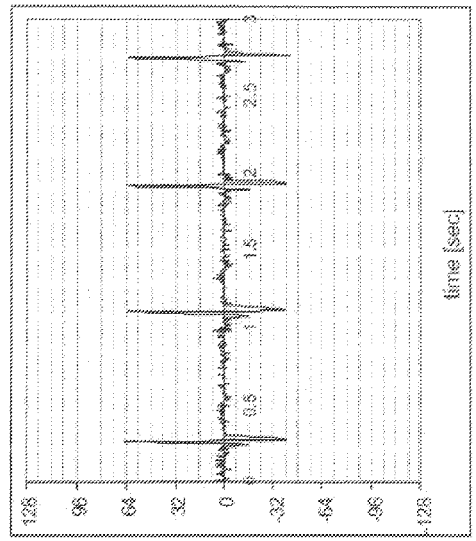
Fig. 3A
Fig. 3B
Fig. 3C

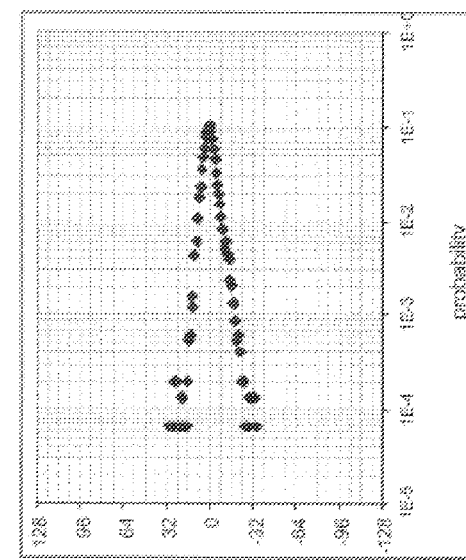
Fig. 7C
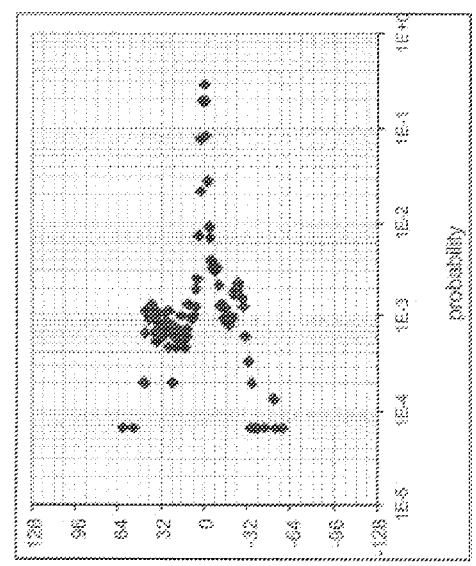
Fig. 7A
Fig. 7D
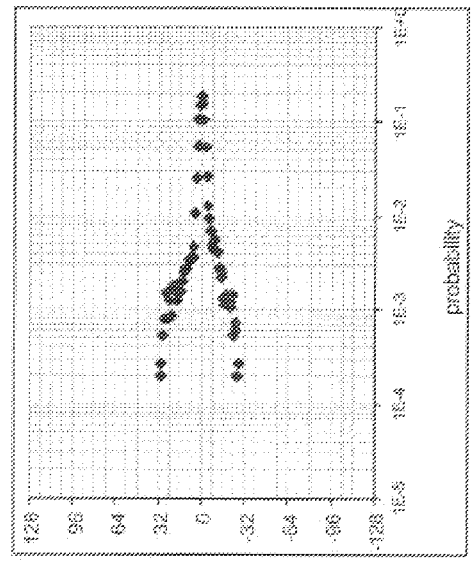
Fig. 7B

SYSTEM AND METHOD FOR SMOOTHING SAMPLED DIGITAL SIGNALS

RELATED APPLICATION

This application is a continuation of U.S. patent application Ser. No. 11/691,115, filed Mar. 26, 2007 entitled "SYSTEM AND METHOD FOR SMOOTHING SAMPLED DIGITAL SIGNALS", herein incorporated by reference in its entirety.

BACKGROUND OF THE INVENTION

The present invention relates to data storage and processing and in particular data storage and processing with data obtained from an implantable medical device.

DESCRIPTION OF THE RELATED ART

There are numerous implantable medical devices (IMDs) used to provide various therapies or collect data that is useful in evaluating and providing care for a patient. Common cardiac IMDs would include implantable pulse generators (IPGs) or pacemakers, implantable cardiac defibrillators (ICDs) which often include pacing capabilities, devices sensing other cardiac parameters such as pressure or impedance, implantable loop recorders (ILRs) which collect data but do not necessarily provide any therapy function, or any combination. Beyond cardiac devices, IMDs are commonly used in a wide variety of other applications. For example, neurological devices may stimulate or gather information from the brain or portions of the nervous system. Devices may be provided to monitor glucose levels and dispense insulin. The use and applicability of IMDs is constantly expanding into additional anatomical and physiological fields.

While the various IMDs may be quite different in form, function, and operation there are certain characteristics that will apply generally. As the device is implanted within the patient (and generally not readily accessible), such a device should be reliable, self sustaining for an appropriate period of time, and when appropriate, have the ability to communicate with other implanted devices or devices external to the patient. Certain desirable characteristics will tend to compete against one another. For example, minimizing the size of a given device is generally preferred; however, this in turn limits the space available for internal components. Similarly, there is a preference to have as many features or functions as possible; but these taxes the already limited resources in terms of power consumption and internal components.

Information or data is in some form a physical construct that behaves and can be manipulated according to certain laws, regardless of the particular storage medium or mechanism. In fact, information can be discussed in terms of scientific principles such as thermodynamics, quantum mechanics and the like. In particular, the concept of entropy from the second law of thermodynamics is useful in describing quantities of non-redundant data in a set.

This is useful in that there is a continuing desire to develop and operate IMDs efficiently and effectively, while maximizing the benefit and usefulness of scarce resources. One area often considered is internal memory and information processing. As electronic devices in general, and memory in particular, improve certain benefits are realized in scale within IMDs. However, as more resources become available (e.g., memory) the amount of information expected to be collected and stored increases. Thus, there is a desire to efficiently collect, store and transmit data with an appropriate degree of reliability.

BRIEF DESCRIPTION OF THE DRAWINGS

FIGS. 3-7 are graphs of waveforms and corresponding probability distributions.

DETAILED DESCRIPTION

Figure 1:
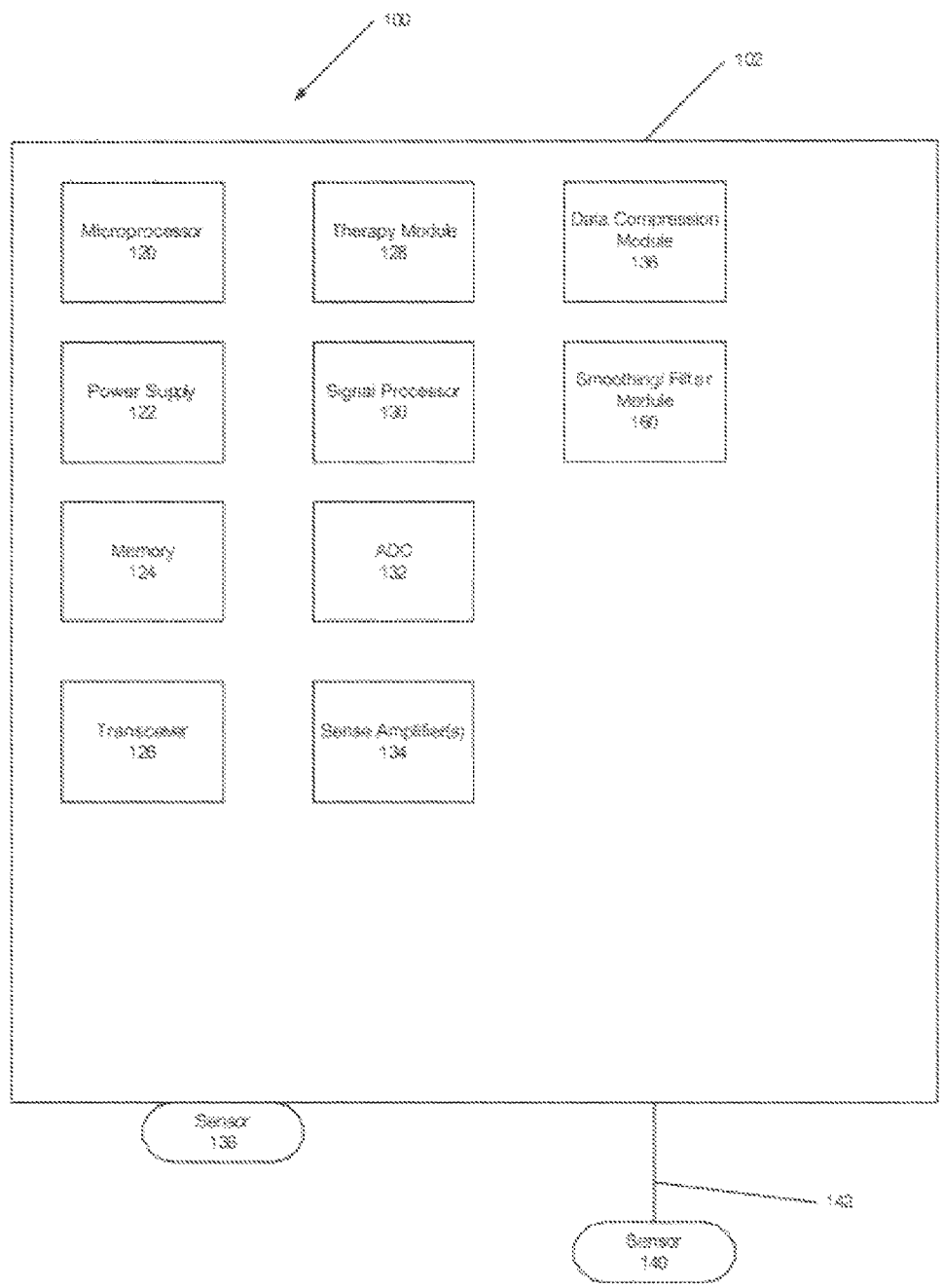
FIG. 1 is an illustration of an IMD consistent with the principles of the present invention.

FIG. 1 is a block diagram illustrating some, but certainly not all of the components of a typical implantable medical device (IMD) 100. The construction, operation, usage and implementation of various IMDs is generally known and FIG. 1 is provided simply for illustrative and non-limiting purposes.

The IMD 100 includes an appropriate housing 102 enclosing the various components. One or more microprocessors 120 are typically provided along with a power supply 122 which usually includes a battery and capacitors (for high voltage therapy). One or more memory modules 124 are provided in various forms that may include operating instructions and/or receive and store data collected by the IMD 100. The IMD 100 includes a transceiver 126 that permits two-way communication between the IMD 100 and an external (to the patient) device and/or another implanted device. A therapy module 128 is illustrated and generally includes the components and instructions to provide one or more therapies, if the IMD 100 is so equipped. Examples may include pacing, defibrillation, neural stimulation, drug delivery and so on. A signal processor 130 receives and processes data. An analog to digital converter (ADC) 132 receives a raw or processed analog signal and convert that signal into digital data. The IMD 100 may include on or more sense amplifiers 134 that receive data from one or more sensors 138, 140 and then output the amplified signal to other components within the IMD 100. A given sensor 138 may be coupled directly with the housing 102 or a remote sensor 140 may be coupled via a lead 142 or through wireless communication. To maximize resources, the IMD 100 includes a data compression module 136 that compresses data before storing that data into memory 132. Also included is a smoothing/filter module 160.

When cardiac data, for example, is collected by the IMD 100, it is referred to as an electrogram (EGM) as opposed to surface collected data in the form of an electrocardiogram (EKG or ECG). The EGM data is stored in the memory 124 until it is telemetered out, the IMD 100 is extracted, or the memory capacity is exceeded and the data is overwritten. The IMD 100 includes a finite memory and has a limited power supply; thus, care is taken to minimize any unnecessary power consumption. Under these conditions, the data compression module 136 seeks to optimally compress the data in a lossless manner, when appropriate and in some cases permits a lossy data compression.

Figure 2:
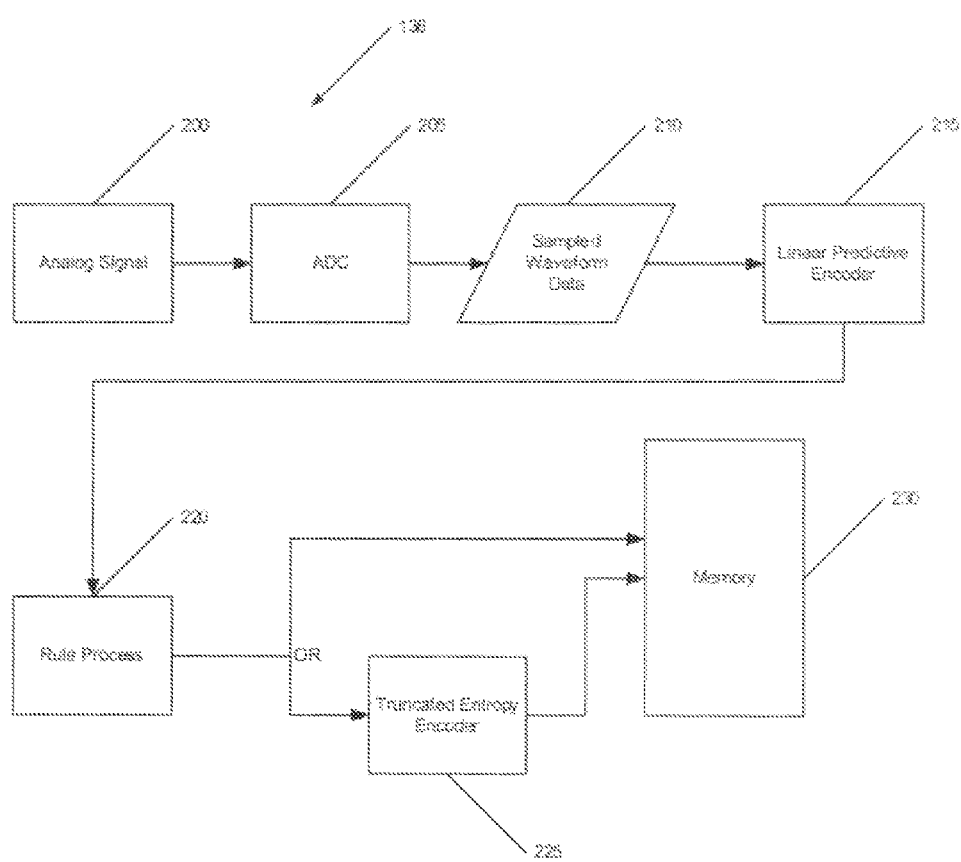
FIG. 2 is a block diagram of a data compression module consistent with the principles of the present invention.

FIG. 2 is a block diagram illustrating data compression module 136. The concepts presented here will be described in general and at a relatively high level as an overview, with a more detailed explanation of certain concepts to follow with reference to subsequent figures. An analog signal 200, such as a cardiac waveform, is obtained and converted into digitized data 210 by the ADC 205 (or ADC 32 of FIG. 1). As is well known, the analog signal is sampled at some predetermined sampling frequency (e.g., 1 MHz) and the value of the waveform is recorded for each sampled point in time. In this example, the value will be a voltage on the order of milivolts. The resolution is defined between rails (upper and lower limits) by the total available increments (typically equal). For example, with 256 discrete increments the above example would be a sample frequency of 1 MHz with 8 bit resolution. 12 bit resolution would provide 4096 increments and so on.

The sampled digital waveform data 210 passes through a linear predictive encoder 215 which acts to simplify the waveform for subsequent processing. This process will be described in greater detail but in short, in one embodiment the derivative of the sampled waveform is obtained. More specifically, the first data point and certain subsequent data points are left intact while the remaining sampled data points are converted into the difference between a given data point and the previous data point. Thus, the first data point remains the sampled value. The second data point becomes the difference between the second sampled value and the first sampled value. The third data point becomes the difference between the third sampled value and the second sampled value. To decode this data, the reverse process is performed. Again, the first data point is intact. The second data point is obtained by adding the difference stored in memory to the first data point and so on.

The linear predictive encoder 215 encodes the data into a form that generates a probability distribution that is generally centered about a zero baseline and has approximately the same shape (despite general variations in original waveforms of the same type) for the highest probability data points. This allows for the subsequent partial application of Huffman encoding which maps certain potential increments or values to a "codeword." By using relatively short codewords for the most frequently used increments (those having the highest probability of use) a first order of data compression is achieved. For example, a codeword representing an 8 bit value might only have 2 bits; thus a compression ratio of 4:1 is achieved. To provide a complete Huffman encoded alphabet for all potential values, some data points will map to significantly longer codewords. With an 8 bit example, one codeword will have 256 bits. Therefore, to achieve an overall compression ratio that is positive, the probability that given data points are obtained is an element that should be known and controlled for; hence an understanding and calculation of entropy. The mapping of codewords to their values is stored in a lookup table in software, hardware or firmware and is available for both encoding and decoding. In FIG. 2 for example, the lookup table could be contained within the linear predictive encoder 215 or stored within memory 124 and accessible by the linear predictive encoder 215. A single lookup table provides the simplest scheme; however, it should be appreciated, that multiple lookup tables may be provided and the appropriate table is selected based upon waveform type, point in time, or some other factor.

Once the derivative waveform data points are obtained, there is an optimal band wherein the mapped codewords are equal to or shorter than the data they map to (e.g., 8 bits or less). Outside of this band, the codewords are longer than the data they represent (e.g., 9 bits or longer with our 8 bit example).

To summarize, in an 8 bit resolution example, each data point sampled will be 8 bits long; in order to achieve data compression, codewords having less than 8 bits must be used for at least some data points. If shorter codewords were always used then every data point would achieve compression; however, in order to provide codewords for all potential data points, some of these codewords become very long. By selecting the codewords so that the most likely data points have the shortest codewords and the longer codewords are assigned to unlikely data points, the overall data scheme achieves compression, when properly mapped with probability. Further analyzing the derivative data, it is possible to determine which data points/codewords are equal to or less than the current bit rate (e.g., 8 bits or less).

The data parsed by the linear predictive encoder 215 is subjected to a rule processor 220 that evaluates whether, at a high level, the current data point is inside or outside of this optimized band. If the data is within the optimized band, then the codewords are substituted for the data by the truncated entropy encoder 225 and stored in memory 230 (which may or may not be the same as memory 124 of FIG. 1). If the data is outside of the band then the codewords are not used; rather, the raw (e.g. 8 bit data) is stored directly in the memory 230. While no compression is achieved for these data points, there is no extra memory usage for what would have been a longer codeword. While achieving good results, actual implementation is somewhat more complex in that both the encoder and separately the decoder need to be able to distinguish between codewords and raw data.

As previously indicated, the process is well suited for IMDs 100 that are attempting to minimize power consumption and data buffering. Thus, one mechanism employed by the rule processor 220 is to determine whether the previous data point should or should not have been encoded. In this approach, the first data point that occurs as a waveform transitions e.g., out of the optimum band, will be encoded even though according to the above logic it should not have been. Thus, when evaluating the next subsequent data point, the rule processor considers whether the previous data point should or should not have been encoded. If the determination is that the previous data point should have been encoded, then the current data point in encoded. Conversely, if the previous data point should not have been encoded, then the current data point is not encoded. As these form definitive rules, the same process can occur during decoding of the data. In this manner, the vast majority of data points are compressed and the lower probability data values are maintained in either their raw length or a modified encoded form which is longer than the raw length, but significantly shorter than some potential encoded values.

FIGS. 3-7 illustrate various sampled waveforms, derivatives of those waveforms and probability distributions for the waveform and derivative waveforms. FIG. 3A is a sampled waveform of a cardiac EGM from a normal sinus rhythm. FIG. 3B is the derivative of the waveform of 3A, wherein the first data point remains unchanged but each subsequent data point becomes the difference between the current data point value and the previous data point value. As a simple numerical representation, the sample waveform data will have data points 1, 2, 3, 4, etc. (with each having some measured value for voltage and designated 8 bit value for that voltage). The derivative waveform will have data points 1, (2-1), (3-2), (4-3), etc.

This is referred to herein as linear predictive encoding. That is, a model or an equation is established. For each data point the model will provide an expected or predicted value. The actual data point is compared with the predicted value and the difference or error is stored rather than the data point. If a predictive equation were perfect, then the error would be zero (0) for each data point. That is, given the value for the first data point, the model will accurately predict each subsequent data point precisely. As an example, if the waveform were a pure sine wave, its derivative is a cosine; thus, given a starting point or series of initial points each subsequent point is calculated with certainty.

In the real-world cardiac samples, there is no such precise repetitive pattern or available equation to model to achieve certainty in prediction; however, the concept holds. The model used herein is that each data point is equal to the previous data point. Thus, when compared to the model, the difference between the predicted value (i.e., the last data point) and the sampled value is the error for the model and this value is stored. It should be appreciated that while biologic waveforms whether cardiac, EEG, or otherwise are unlikely to be precise, pristine sine waves, various algebraic models may be provided that are more complex than the example above. Furthermore, these models may be non-linear and may consider any number of previous data points in predicting the current value. The more accurate the predictive model, the smaller the error values and the more effective the encoding.

Figure 4C:
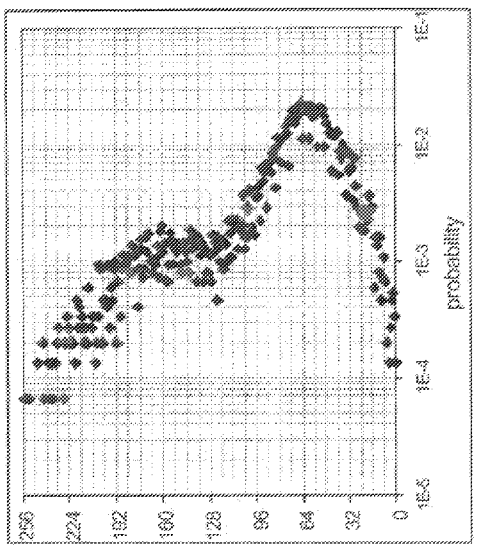
Figure 4A:
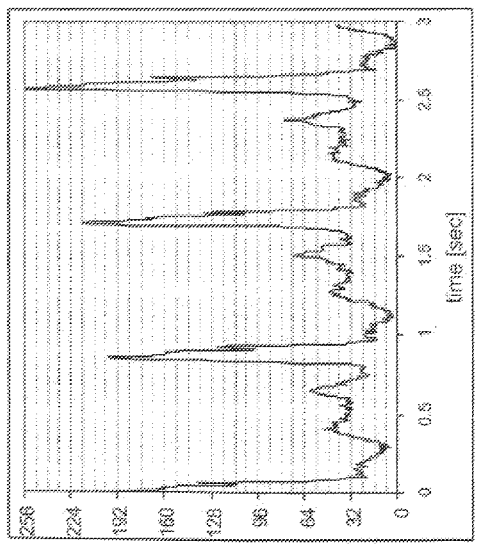
Figure 4B:
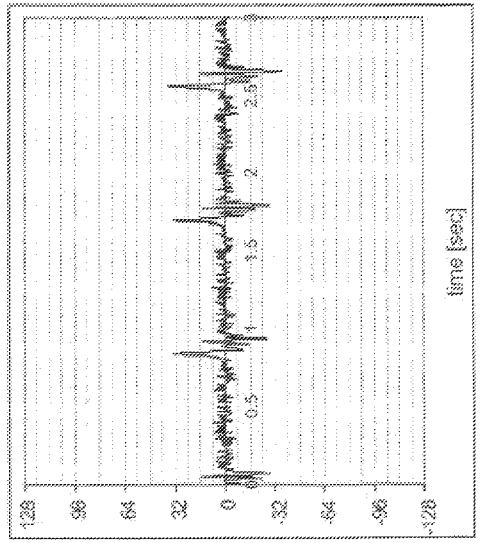
Figure 5C:
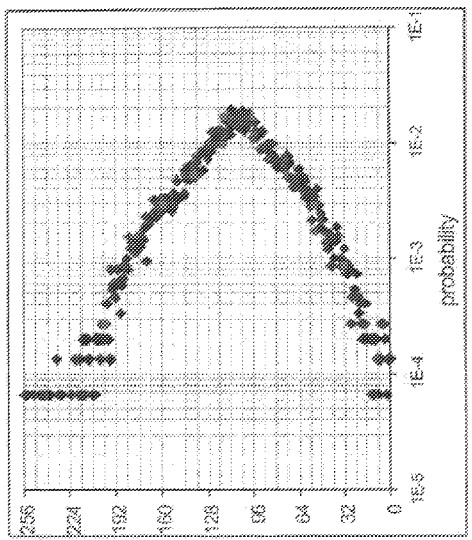
Figure 5A:
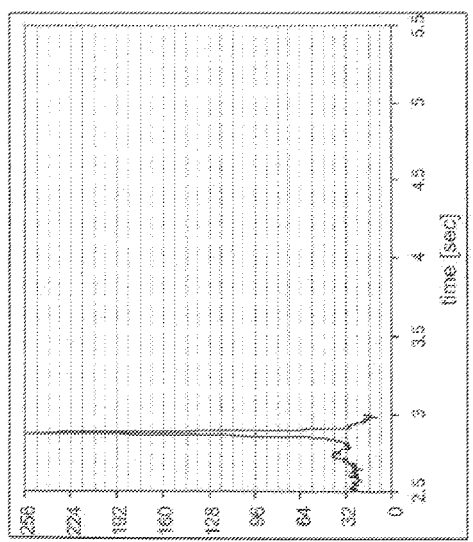
Figure 5B:
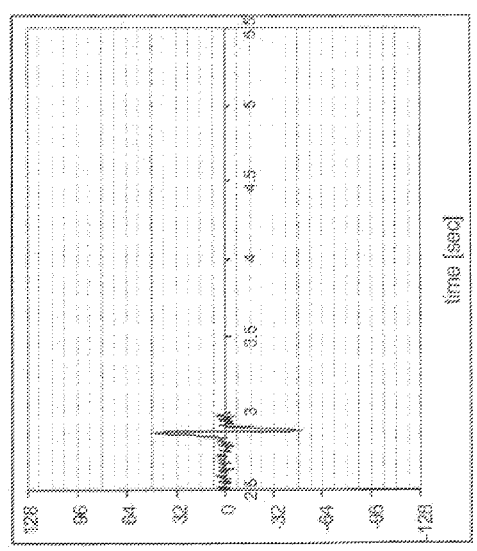
Figure 6C:
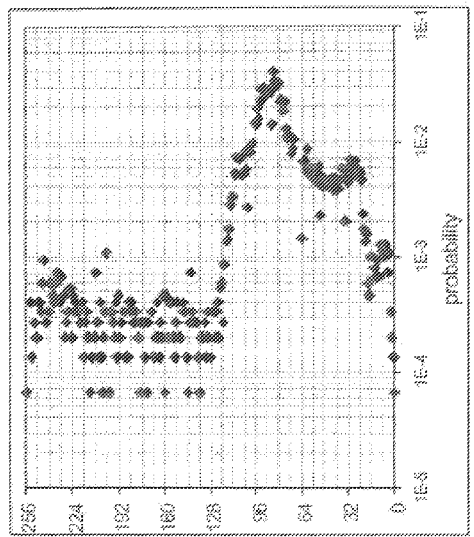
Figure 6A:
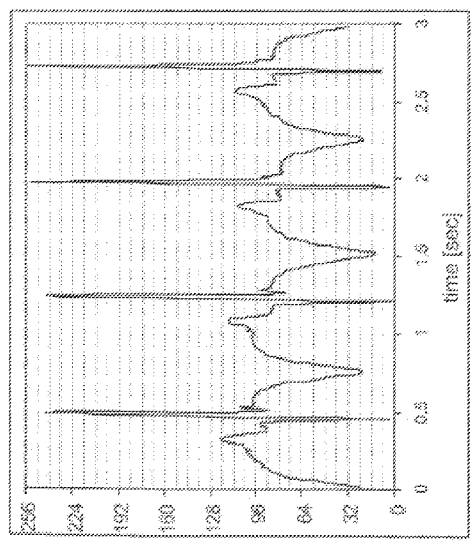
Figure 6B:
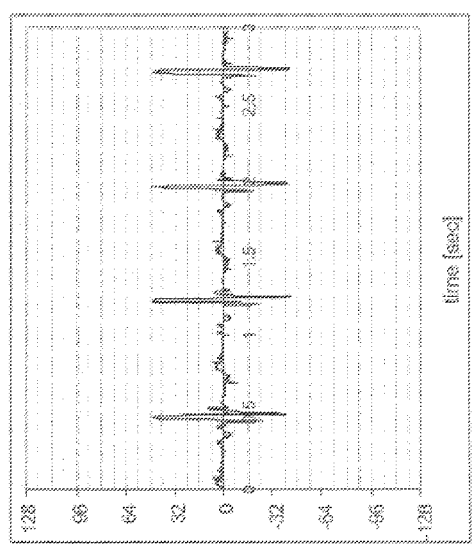

FIG. 3C is a probability distribution of the values of the sampled waveform in FIG. 3A and illustrates why the predictive encoding is useful. The X axis represents probability (number of occurrences) with higher probabilities corresponding to larger X values. The Y axis is the increment (bit value). As these examples utilize an 8 bit resolution, there are 256 increments or potential values. These correspond to a voltage value. A probability distribution such as that of FIG. 3C allows for Huffman encoding to achieve effective results. That is, in order to optimize Huffman encoding, the actual probability distribution must be known. As just indicated, FIG. 3C is in fact the actual probability distribution of the waveform of FIG. 3A. Unfortunately, FIG. 4A is a sampled waveform from a patient with congestive heart failure and FIG. 4C is the corresponding probability distribution. FIG. 5A is a sampled waveform taken during ventricular fibrillation and FIG. 5C is the corresponding probability distribution. FIG. 6A is a sampled waveform taken during ventricular tachycardia and FIG. 6C is the corresponding probability distribution.

In comparing the illustrated probability distribution graphs (FIGS. 3C, 4C, 5C, 6C) it becomes apparent that they are quite distinct. The peaks are each centered about a different value; their shapes are different and the values assigned are very different. This is readily apparent for distinct types of cardiac waveforms; however even if other samples of similar waveforms (e.g., normal sinus rhythm) were compared there would be substantial variation within a given patient and more so between various patients in the population. As effective Huffman encoding requires that the probability distribution be known (so that codewords can be assigned) a priori and stored in memory as a lookup table, the variance in waveform probability distributions illustrates a challenge.

FIGS. 7A-7D are probability distribution graphs of the derivative waveforms (FIG. 3B, 4B, 5B, 6B). While not identical, they are substantially more similar than the previous probability distributions. Further, each probability distribution is uniformly centered about zero (0) and the most probable values fall within a relatively narrow band of values. This would still not provide for an optimum Huffman alphabet for all potential values for all waveforms.

Figure 8:
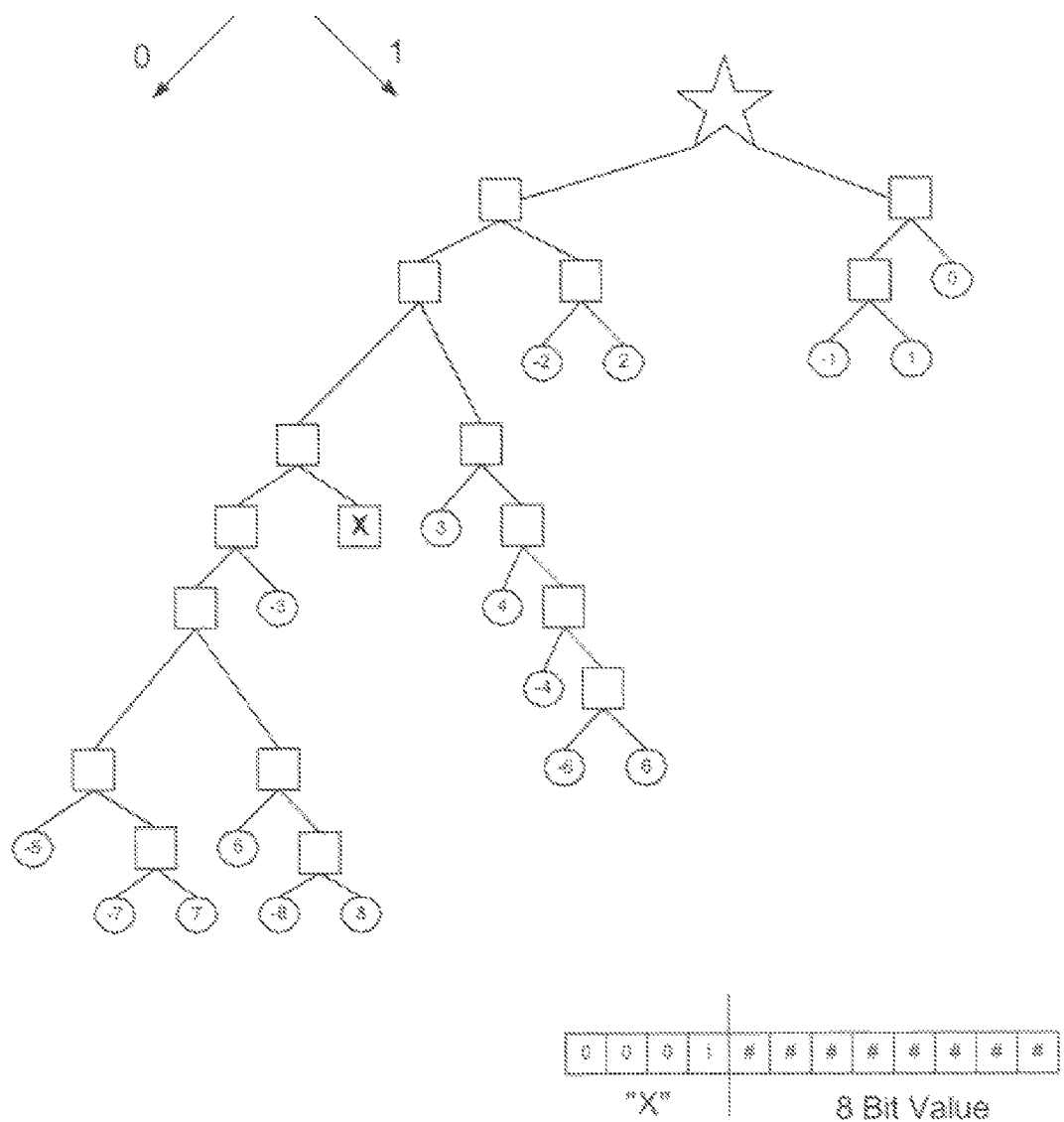
FIG. 8 is a schematic diagram illustrating a truncated encoding tree.

FIG. 8 is a graphical representation of a truncated encoding tree according to one embodiment consistent with the teachings of the present invention. The star illustrates the starting point or starting node. Each oval represents the decimal equivalent of the indicated 8 bit (for this example) value and includes the set {0, −1, 1, −2, 2, −3, 3, −4, 4, −5, 5, −6, 6, −7, 7, −8, 8). Each square node is a junction and each line indicates a bit value (0,1) depending upon direction. In this example, a line moving towards the left indicates a "0" and a line moving towards the right indicates a "1" with movement recognized from a higher position to a lower position, as illustrated. This convention is arbitrary and the reverse could be used instead (left is "1"; right is "0").

This truncated coding tree provides the "codeword" for a given value. Thus, if the value to be encoded equals "−3" the codeword would be "00001". Starting from the star, there are 4 leftward lines and one rightward line until the oval with "−3" is reached. Thus, for a particular data point of the derivative waveform, the value may be "−3" and "00001" is encoded into memory. This is a 5 bit data point as opposed to an 8 bit data point as would normally be used. That is, assuming 0 is set to "128" on a 256 bit scale, then "−3" would normally be the binary value for "125" or "01111101". As the derivative waveform represents changes from one data point to the next, the values will usually be relatively small. The encoded value for "0" is "11"; the encoded value for "1" is "101" and so on. As these are the most probable values they have the shortest codewords and achieve the greatest compression ratios.

As identified with reference to FIGS. 7A-7D, the most probable values (those further to the right on the X axis) fall within a relatively narrow band. This is generally captured by using values from −8 to 8; which corresponds to our 8 bit example. Thus, in a 12 bit example, the tree would encode values from −12 to 12. Therefore, the most probable and most frequently used values will have a codeword assigned. It should be appreciated that the values populating the tree are taken from the sample probability distribution. While taking the derivative waveform centers the probability distribution about zero, the values used are likely to be commonly employed. Of course, there may be various embodiments wherein the most probably values differ from those illustrated and the tree will be populated with those values instead.

Another aspect of the codewords defined by the tree is that they are prefix free. That is, for this example, the 18 assigned codewords are unique and unambiguous. The codewords will vary from 2 bits to 8 bits and it would not be possible to decode a value from a variable length codeword in a stream of data absent this aspect. For example, according to FIG. 8, if a codeword begins with "1" it can only represent {0, −1, or 1}. "11" can only represent "0"; "101" represents "1"; and "100" represents "−1". As such, "10011" could not be a single codeword because it would be ambiguous whether that data set indicated the single codeword or represented "−1" followed by "0". When decoding the data, it is parsed until an unambiguous codeword is identified and the next bit begins the next codeword.

As illustrated, codewords are provided for the decimal values of −8 to 8. In a 256 bit example, the maximum difference between two adjacent data points could in fact equal 256 ((128−(−128)=256). As a practical matter, the waveform is unlikely to swing that dramatically from point to point. Nevertheless, point to point variations will likely exceed 8 at times. The tree could be extended to provide codewords for all 256 values; however, in order to be unambiguous these codewords would become increasingly large with the largest having 256 bits. Hence, the present embodiment utilizes a truncated entropy encoder. That is, for any value not displayed on the tree, the actual 8 bit value is utilized with a prefix or exit code which is the codeword indicated by the "X" oval on the tree. This means that these data points will be encoded as 12 bit values. During decoding, the codeword for "X" is recognized and the decoder then takes the next 8 bits for the data value. The data is parsed as discussed above beginning with the $9^{th}$ bit. This means that the system has utilized 12 bits to store an 8 bit value which is negative compression factor. On the other hand, 12 bits is the maximum length for any value and is significantly less than many of the codewords that would exist for a fully expanded tree. This combined with the lower probability of using values needing a codeword prefix results in an overall positive data compression.

To summarize, the truncated entropy encoder illustrated by FIG. 8 indicates that codewords are provided for less than the complete set of potential data increments; thus the tree or data map is truncated. The codewords themselves are unambiguous, prefix free and one codeword is utilized to signal that a predetermined number of bits to follow are unencoded. In the illustration of FIG. 8, this is represented by the populated 4 bit "X" value and the 8 bit place holder. This X node or value will be referred to as the prefix codeword. It should be appreciated that in other protocols, different values may be encoded depending upon probability and the X node may be provided at a different node either increasing or decreasing the required number of bits for the prefix codeword. Furthermore, systems using different resolution (e.g., 12 bit encoding) may be used with or without a corresponding expansion of the tree. It should also be appreciated that various combinations, while not illustrated, may be employed. For example, other unique codewords could be created that indicate longer or shorter data to follow; or that other action is to be taken, such as error checking or the like.

Figure 9:
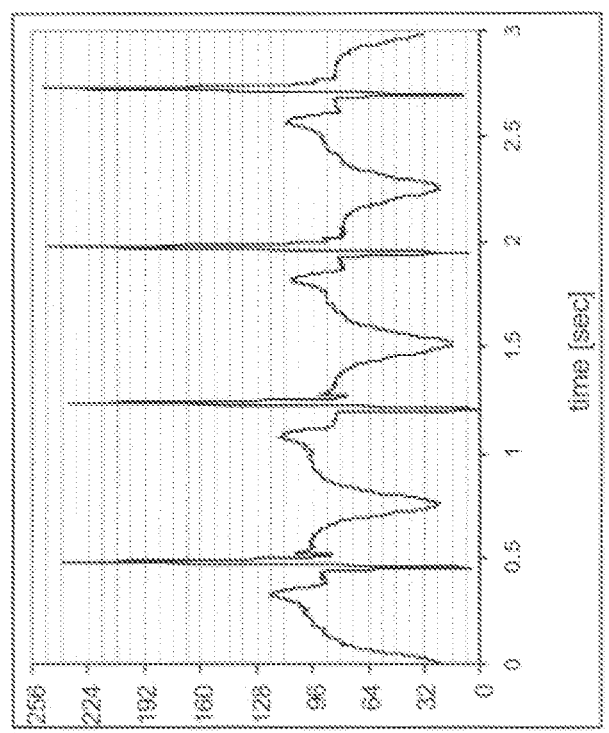
FIG. 9 is a graph of a sampled waveform.
Figure 10:
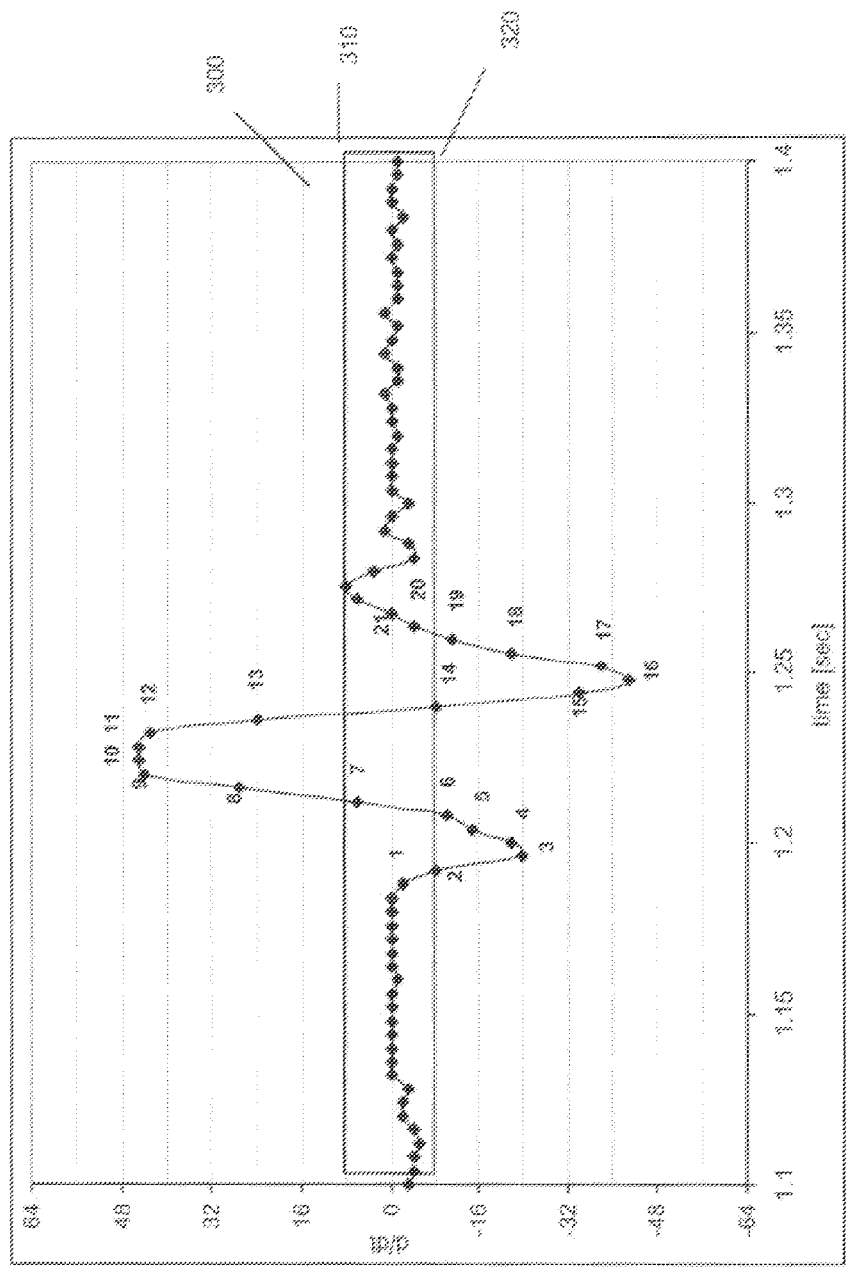
FIG. 10 is an expanded view of a portion of the waveform of FIG. 9.

FIG. 9 is a waveform sample from a patient during ventricular tachycardia. FIG. 10 is a small portion (a QRS complex) of the derivative of the waveform of FIG. 9 and illustrates (as diamonds) the various points that are digitally sampled. This example continues to use the 8 bit resolution and truncated tree illustrated in FIG. 8; though this is non-limiting. For illustrative purposes, a high probability band 300 is bounded by an upper limit 310 and a lower limit 320 and is centered about zero. The high probability band 300 simply visually indicates that any data point falling on or in that band will have a codeword for its value; thus, in this case the upper limit 310 is equal to 8, while the lower limit 320 is equal to −8.

A few of the enumerated data points will be explained to describe the process. Initially, numerous samples are collected that fall within the band 300 prior to data point 1. As previously discussed, the first data point stored is stored unencoded and has the value from the actual waveform, not the derivative. To avoid perpetuating any errors, this process is repeated periodically. For example, after every 200 samples the process may be repeated so that another unencoded waveform data point is stored. The frequency of this error prevention can be selected as desired and may be based on a number samples, periods of time, distinct events, other error checking parameters or any other convention that may be employed by both the encoder and the decoder. As data is decoded sequentially, an error in a bit will propagate through and corrupt the remaining data in the set. Periodically sending an unencoded data point will restart the process and prevent this propagation.

With the present example in FIG. 10, data point 1 will be presumed to be an encoded data point. For data point 2, the rule processor 220 evaluates data point 1 to determine whether data point 1 should have been encoded. Data point 1 was within the band 300 and should have been encoded. Thus, data point 2 is encoded by the encoder 225. Data point 2 appears to have the value of negative 8, thus the codeword would be "00000110", which is stored in memory 230. For data point 3, the rule processor 220 evaluates whether data point 2 should have been encoded. As data point 2 fell on or in the band 300, data point 2 should have been encoded. Thus, data point 3 is encoded even though it is outside of the band 300. To encode data point 3, which has a value of about −24, the prefix codeword is employed ("X+8 bit value for −24 (or 104)) which in this example is "00011101000." This value is stored in memory 230 by the entropy encoder 225. For data point 4, the rule processor 220 evaluates whether data point 3 should have been encoded. Data point 3 was encoded, but should not have been in that in fell outside the band 300. Thus, data point 4 is not encoded. Here the rule processor 220 stores the 8 bit value of data point 4 directly in memory 230, bypassing the entropy encoder 225 (of FIG. 2). When acting upon data point 7, the rule processor 220 determines whether data point 6 should have been encoded and it should not have been (and was not); thus, data point 7 is not encoded despite falling within the band 300. Data point 8 will be encoded because data point 7 should have been; thus, data point 8 will have a 12 bit value. Similarly, data point 14 will not be encoded because data point 13 should not have been. Here, there is no net loss as the codeword would have an 8 bit value; thus, using the actual 8 bit value is equivalent.

This process is referred to herein as linear predictive entropy encoding (LPEE); that is, determining whether to use entropy encoding based upon the results of the previous data point. There is only a loss of compression (no loss of accuracy or resolution) when a 12 bit value is used where an 8 bit value or smaller could have been used or an unencoded 8 bit value is used where a codeword of less than 8 bits could have been utilized.

The following table is presented for each of the enumerated data points, which is a sample set selected arbitrarily for illustrative purposes only.

| Current Data Point | Last Data Point | Should last be encoded? | Encode Current? | Good/Bad? | Result w/out (LPEE)* |
|---|---|---|---|---|---|
| 1 | — | y | y | good | g |
| 2 | 1 | y | y | good | g |
| 3 | 2 | y | y | bad | b |
| 4 | 3 | y | n | good | b |
| 5 | 4 | n | n | good | b |
| 6 | 5 | n | n | good | b |
| 7 | 6 | n | n | bad | g |
| 8 | 7 | y | y | bad | b |
| 9 | 8 | n | n | good | b |
| 10 | 9 | n | n | good | b |
| 11 | 10 | n | n | good | b |
| 12 | 11 | n | n | good | b |
| 13 | 12 | n | n | good | b |
| 14 | 13 | n | n | bad | g |
| 15 | 14 | y | y | bad | b |
| 16 | 15 | n | n | good | b |
| 17 | 16 | n | n | good | b |
| 18 | 17 | n | n | good | b |
| 19 | 18 | n | n | good | b |

-continued

| Current Data Point | Last Data Point | Should last be encoded? | Encode Current? | Good/Bad? | Result w/out (LPEE)* |
|---|---|---|---|---|---|
| 20 | 19 | n | n | bad | g |
| 21 | 20 | y | y | good | g |
| Ratio of bad or b to total | | | | 6/21 | 15/21 |

Good = coded for values in band or 8 bit data for values out of band
Bad = 12 bit values (Prefix codeword + 8 bit data)
g = 8 bit or less
b = 12 bit
*results if all data points used codewords, including X prefix so maximum is 12 bit in current example
The terms "good or bad" are not meant to indicate a positive or negative attribute, but only whether the optimum bit size is utilized In this example, approximately 76 data points are illustrated with only 15 falling outside of the band 300. Thus, over 80% of the data points fall within the band 300. While only illustrative and non-limiting (in fact an arbitrarily selected waveform sample and length), the use of linear predictive entropy encoding on this sample reduced the use of 12 bit words by approximately 43%.

As previously indicated, there is substantial variation that occurs in encoding, compressing and storing data from various waveforms. The waveforms themselves may be quite distinct from one another to begin with and the codewords employed vary in length and their use is based upon probability. As an example, with the previously described exemplary waveforms, sampled at 251 Hz with 8 bit resolution, the above described truncated entropy encoding embodiment provides for an average codeword length of 3.4 for the normal sinus rhythm, 4.4 for atrial fibrillation, 3.9 for congestive heart failure and 3.4 for ventricular tachycardia. The shortest codeword will be 2 bits and the longest will be 12 bits. These are presented for illustrative purposes and not meant to be limiting. When the rule based processor is added, the average values will decrease as many of the previous 12 bit codewords will be replaced by 8 bit values.

Thus far, there has been an assumption that the waveform spanned the entire dynamic range of the sampler. When this is not the case, the performance of the encoding will improve even more. That is, higher, absolute value differentials will occur less frequently. With waveforms that span about 50% of the range of the sense amplifier, the lossless compression rates may be 4:1.

The embodiments described may be effectively utilized on streamed or real-time data to achieve good data compression ratios while providing lossless data storage. Cardiac EGM data is effectively and efficiently stored in a reliable, real-time manner that allows for high resolution reconstruction of the sampled waveform. Other physiological signals are also well suited for this type of encoding. For example, cardiac pressure data is typically cyclic and falls within a narrow dynamic range. Significant variation occurs when the patient changes environments (e.g., moves to a high altitude) and these infrequent variations are effectively managed by using the predictive linear encoding. Thereafter, the truncated entropy encoding may be used to achieve high compression ratios. It should be appreciated that any physiologic waveform or any waveform in general may be stored using the embodiments described herein.

In some embodiments, the truncated encoding tree (FIG. 8) is defined and stored in memory in both the encoder and the decoder. Similarly, the rule or algorithm for the linear predictive encoding is defined and stored in memory. For example, the current data point is assumed to be equal to the previous data point; the actual difference between the two (i.e., the error) is the value stored in memory. While both the encoder and decoder need to have the same tree and rule(s); neither the tree nor the rule(s) necessarily must remain static. That is, adaptive Huffman encoding may be utilized to develop a patient specific tree based upon sampled data. Furthermore, this tree may be periodically changed based upon sampled data; therefore, the tree is dynamically changed as the underlying probability distribution changes. For example, a new or updated tree may be generated after several thousand samples and passed to the decoder as appropriate. Similarly, the linear predictive encoding rule(s) cold likewise be generated on a patient specific basis or updated dynamically. That is, as the sample data is collected and processed, a more accurate (i.e., smaller error values) rule (linear or non-linear) is derived. The new rule is then used on data subsequently collected.

The dynamic creation and modification of the tree as well as the predictive encoding rule(s) would be most applicable in embodiments where the underlying signal may vary from source to source (e.g., patient to patient) but has some regularity or pattern within a given source over a useful time period. As explained, cardiac signals even within a single patient will likely have too much variability to benefit significantly from such dynamic modification, particularly on a real-time or streaming basis. However, in other contexts the dynamic modification could be utilized to increase compression of the data.

Thus far, data that is stored in memory represents a sampled data point, an encoded data point, or an entropy encoded codeword for the same. That is, the stored value ultimately reflects a given sampled value of the relevant waveform. It should be appreciated that many other types of data may be stored by a device separate from the sampled waveform. In addition, various indicators or markers may be interleaved with the encoded data.

For example, in various cardiac devices manufactured by the assignee of the present application, MarkerChannel™ data is created and recorded by the device as an annotation of the events occurring within the sensed data. The events may be routine, such as a sensed atrial depolarization (A sense/P wave); a sensed ventricular depolarization (V sense/R wave); paced atrial event (AP); or paced ventricular event (VP). In addition, longer cardiac events such as, for example, atrial fibrillation (AF), ventricular tachycardia (VT) or the like are detected by the device through various algorithms. The initiation of theses events or at least when they are initially detected may likewise be annotated. The annotation of the data is performed by the microprocessor 120 (FIG. 1) based on the data collected, in analog form or at any stage of the digital signal processing.

Each device will typically record multiple channels of data. There may be an atrial channel sensing atrial events, one or two ventricular channels directly sensing ventricular events; other vectors between a given lead/electrode and an electrode positioned within the housing of the device (e.g., right ventricular ring electrode to housing); and any number of other sensed parameters such as pressure or impedance. Typically, the annotation data is stored within the recorded data stream for each channel. If the annotation data is stored separately, it must be correlated in time to the sensed data which requires additional memory usage. In order to identify the annotation, an exit code is provided. For example, with 8 bit resolution and 256 discrete intervals value "256" may be designated as the exit code. Thus, a sampled value that would equate to the interval 256 is assigned to 255; in other words values sensed at, e.g., the voltage corresponding to interval 256 are essentially rounded to the voltage of interval 255. This simply frees up one value to be used as the exit code.

When the exit code is stored, this indicates that a predetermined amount of data following the code is the annotation data. This might simply be a single word mapped to a predefined annotation, such as a V sense, A sense, etc. In this manner, minimal memory is expended and the annotation is correlated in time with the event in the relevant waveform.

Figure 11:
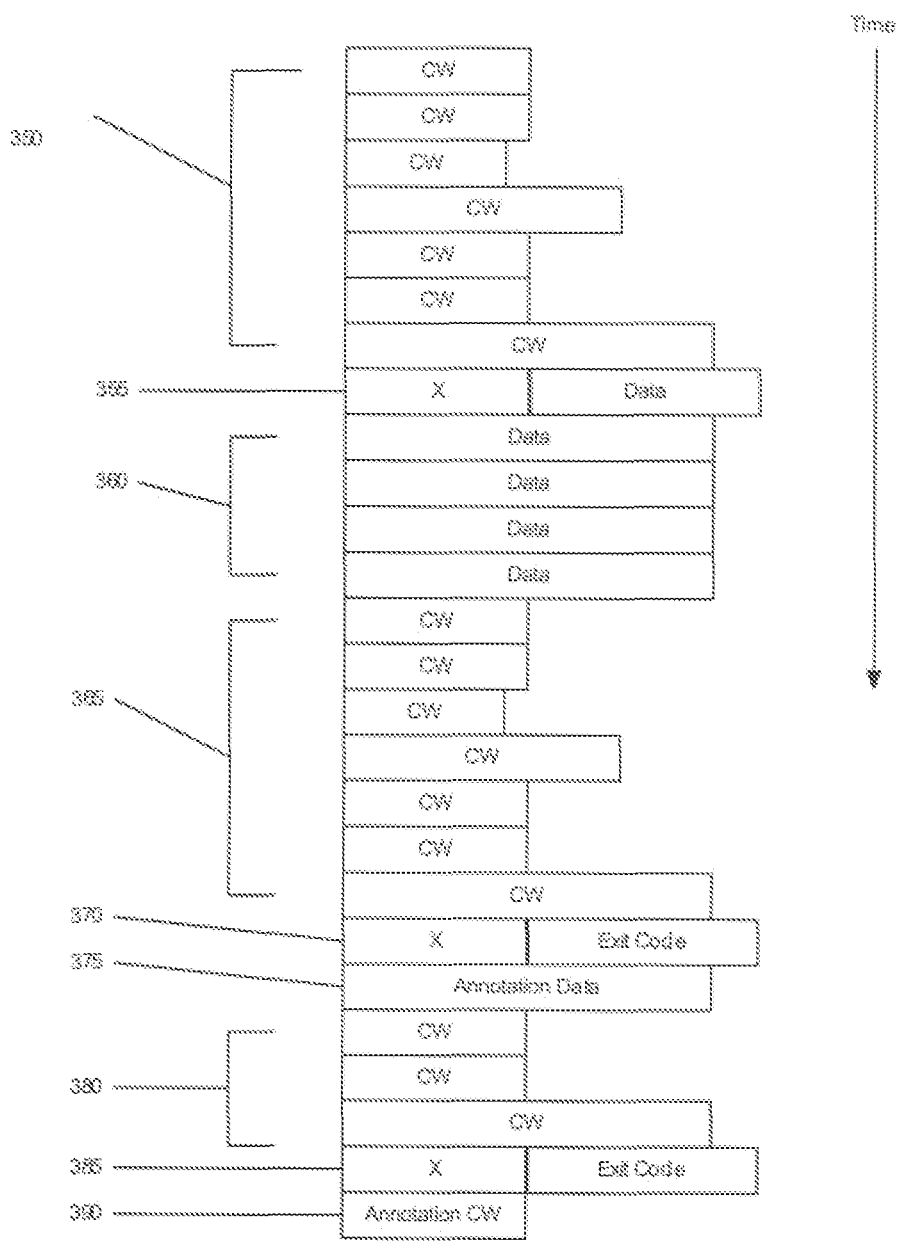
FIG. 11 is a schematic diagram of sequentially stored data.

FIG. 11 is a block diagram illustrating sequentially stored data points in memory. Initially, there are a series of data points encoded as variable length codewords 350. Data point 355 is an "X" codeword followed by an, e.g., 8 bit data value. Next, there are a series of non-entropy encoded data points 360, followed by another series of data points encoded as codewords 365. This simply represents a sample of the linear predictive encoding and entropy encoding as previously described.

The data point 370 is the X codeword, again signifying that the data to immediately follow is not entropy encoded. Here, rather than providing an 8 bit sampled data point, the exit code is provided. This signifies that the next stored data point (or series of points) is an annotation, such as MarkerChannel™ data. The annotation data point 375 is provided and signifies a particular event has occurred, started, or stopped at this point in time or may be used to indicate any information relevant in time as determined by the algorithms stored within the device. Using an 8 bit example, with a single word defining an annotation there are 256 possible annotations. Of course, by using more that one word, more annotations are possible. In this manner, the prefix codeword from the truncated entropy encoding tree (FIG. 8) is used in combination with an exit code to indicated interleaved annotations.

Continuing with the stored data, another series of codewords 380 is provided. Another prefix codeword 385 is stored, followed by the exit code indicating annotation data is to follow. In this example, the annotation 390 is a codeword selected from the truncated entropy encoding tree (FIG. 8). As the data recorded at this point is now known to be an annotation, the particular values utilized to represent the annotation may be mapped accordingly. Thus, rather that using an 8 bit value a codeword may be mapped to a given annotation. This will allow shorter values to be stored as annotations, which may be beneficial when certain annotations occur frequently. Using only the truncated entropy encoding tree will produce less possible annotations (e.g., 18), which may or may not be sufficient. The same process may be utilized with the annotations as with the remaining data points. That is, codewords may be utilized for frequent annotations and the combination of the prefix codeword followed by a full-length word may be used for any other annotation not defined by the truncated entropy encoding tree. In such a situation, the prefix codeword (X), would be followed by the annotation exit code. The next data point would either be just a codeword (as illustrated) or another entry of the prefix codeword followed by the annotation data. This would represent a longer value (e.g., 12 bits in the 8 bit resolution example), but would be offset by the repetitive use of short codewords at other times.

As indicated, the relevant device, such as IMD 100 not only collects/samples the waveforms and records some or all of this data into memory, it also analyzes the data to identify events. This may occur whether or not the data is annotated. Returning to FIG. 10, another embodiment of the present invention will be described. What is illustrated is a derivative of a sample QRS complex recorded from a single channel. As previously indicated, this is an arbitrary selection, centered on the QRS with a portion of the PQ segment and a portion of the ST segment illustrated. In processing such a waveform, the IMD 100 may identify the peak of the R wave (point 10, 11) as a means of detecting a ventricular event. Once so identified, other aspects of the complex may be measured, such as the QRS width. Alternatively, the initial deflection may be detected (e.g., points 3, 4) to initially identify the ventricular event. Regardless of the specific mechanism, the complex is detected and if appropriated, annotated.

Of the arbitrary sample selected, the majority of the data points fall within the optimum band (310, 320) and are generally stored with a codeword. The QRS complex itself spans beyond the optimum band (310, 320) but is the most clinically interesting feature. In one embodiment, consistent with the teachings of the present invention, the entropy encoding compression is disabled upon the detection of one or more events, such as an atrial sense, atrial pace, ventricular sense, ventricular pace, or the onset of particular rhythms such as ventricular fibrillation or tachycardia. Whatever the process the IMD 100 identifies such events will be utilized to disable the entropy encoding compression. The compression will be disabled for a predetermined period of time relevant to the event, such as an averaged measured QRS duration for a given patient or an average value for a patient population. Alternatively, compression may be disabled for a predetermined number of samples or until the event concludes, as actually sensed by the device.

In this manner, the data points compressed generally all fall within the optimum band. The data points occurring during the events are not compressed, but there is also no need to use the prefix codeword, thus avoiding combinations that exceed the normal resolution value (e.g., avoid 12 bit word length for 8 bit data point). Depending upon the nature of the signals processed, disabling compression when an event is detected may or may not result in a better overall compression and use of such a feature is selected accordingly. It should be appreciated that with multi-channel recording, a given event such as an atrial sense might only be sensed on one channel (e.g., the atrial lead). Thus, the other channels would continue to be compressed when this is the case, with only the relevant channel(s) disabling compression.

Figure 12:
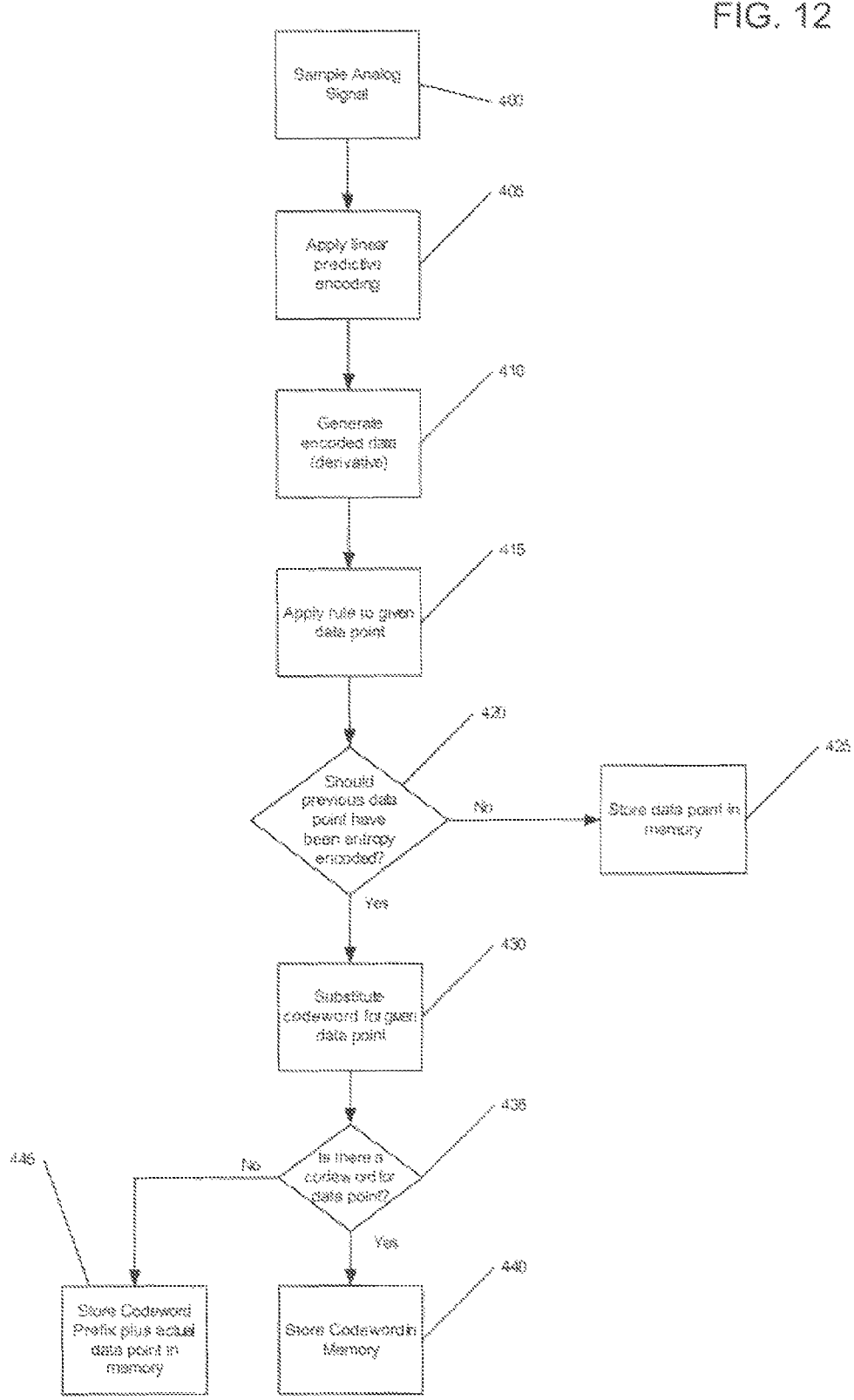
FIG. 12 is a flowchart of a process consistent with the teachings of the present invention.

FIG. 12 is a flowchart describing one method consistent with the teachings of the present invention. The relevant device, such as an IMD 100 obtains an analog input representing a physiologic waveform. The device samples 400 this signal to obtain a digital representation of the waveform according to the parameters of the ADC being utilized. The digitized data is then subjected to linear predictive encoding 405. It should be appreciated that this may be occurring on a real time (data point by data point) basis or by buffering a certain amount of data. The linear predictive encoding 405 generates 410 a derivative of the sampled wave form. Thus, the first data point is left unchanged. Subsequent data points are replaced with a value equal to the difference between that data point and the value of the previous data point. At predetermined intervals, another data point is left intact to prevent the propagation of errors.

Thus, at this point a data point will be a value representing the sampled digital value of an analog waveform at a specific point in time or a derivative value of a particular sampled point. The data point is next subjected to a rule process 415 which evaluates whether the previous data point should or should not have been entropy encoded 420. If not, then the current data point is stored 425 in memory in an unencoded, uncompressed form (e.g., an 8 bit value as in the above example). Alternatively, if the previous data point should have been entropy encoded, then a codeword is substituted 430 for the value of the current data point. The determination of whether a given data point should or should not have been entropy encoded is based upon whether the previous value fell on or within an optimum band defined by a truncated entropy encoding map.

When a code word is to be substituted 430, the value of the data point (e.g., the "error") is compared with the truncated entropy map and a determination is made 435 as to whether a specific codeword is defined for this value. If so, then that code word is substituted 440 for that value and the code word is stored in memory. If not, then the prefix code word is utilized and the actual data point value (e.g., 8 bit value of difference between current sampled data point and value of immediately preceding data point) is added to or stored after the prefix codeword. Thus, the prefix code word and data point are stored 445 in memory.

To decode, the reverse process is performed. That is data is extracted from a device and decoded. The first value is known to be an unencoded starting value. The device then takes the next data point value and adds it to the first data point value to determine that actual waveform data point. For the third data point, the device determines whether the second data point (e.g., an error value) should have been encoded (based on its value). If so, then the third data point is a codeword and the codeword is decoded into an error value and the error value is added to the reconstructed second data point to obtain the third data point. If the second data point should not have been encoded, then the third data point is an actual value (e.g., 8 bit) and not a codeword. The process continues until the next unencoded data point wherein the process restarts. In this manner, data compression is achieved and the original waveform may be extracted without loss.

Figure 13:
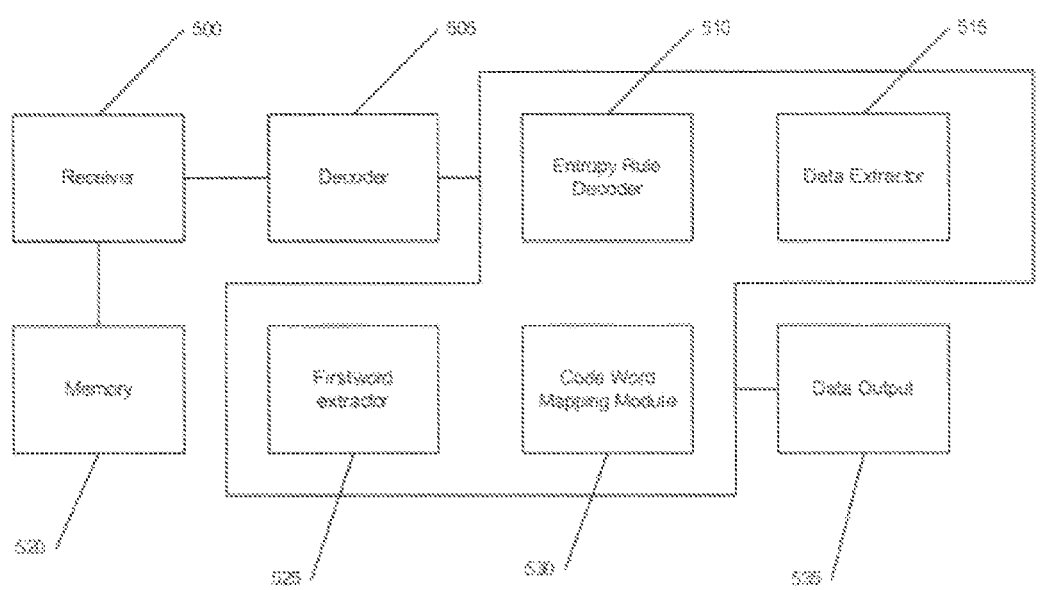
FIG. 13 is a block diagram illustrating a decoding arrangement consistent with the teachings of the present invention.

FIG. 13 is a block diagram illustrating a decoding system. A receiver 500 is provided to receive the stored waveform data. This will typically involved receiving telemetered data from an implantable device either directly or via one or more intermediary devices. The receiver 500 may store data in a local memory 520 for subsequent processing or may send the data directly to a decoder 505 which parses the data. The initial data point and the appropriate subsequent data points are unencoded, non-derivative data of the original sampled waveform and these values are provided by a data output module 535 accordingly. A first word extractors 525 represent the module that identifies the first and subsequent unencoded, non-derivative data. The output from the data output module 535 may be directed to the memory 520 and/or another device for display, analysis or processing.

For the remaining data points, the decoder 505 engages an entropy rule decoder. The entropy rule decoder 510 evaluates the value of a data point (a derivative point therefore representing a difference in value between adjacent data points) immediately prior to the data point currently being evaluated. If this value is such that is should have been entropy encoded, then the entropy rule decoder 510 determines that current data point is an entropy encoded codeword. The codeword is parsed by a codeword mapping module 530 that provides the value from a lookup table for the codeword. This will either provide a value or indicate that the value is contained within the following predetermined number of bits (e.g., a prefix codeword). Either way, a value of the derivative for the current data point is obtained and passed to the data extractor 515.

Conversely, the entropy rule encoder may determine that the previous data point should not have been entropy encoded. Thus, the current data point is not entropy encoded. As such, the value of this derivative data point is an unencoded (i.e., not entropy encoded) value of a predetermined length (e.g., 8 bits). This value is passed to the data extractor 515 accordingly.

The data extractor 515 functions in an opposite manner to the linear predictive encoder. That is, the data extractor 515 receives values for each data point representing its derivative. Thus, to reconstruct the waveform, the derivative value is added to the value of the previous data point to become the actual value for the current data point. The sampled waveform data is thereby reconstructed without loss and provided through data output 535 to memory 520, a display, or another device for manipulation, use or analysis.

Figure 14:
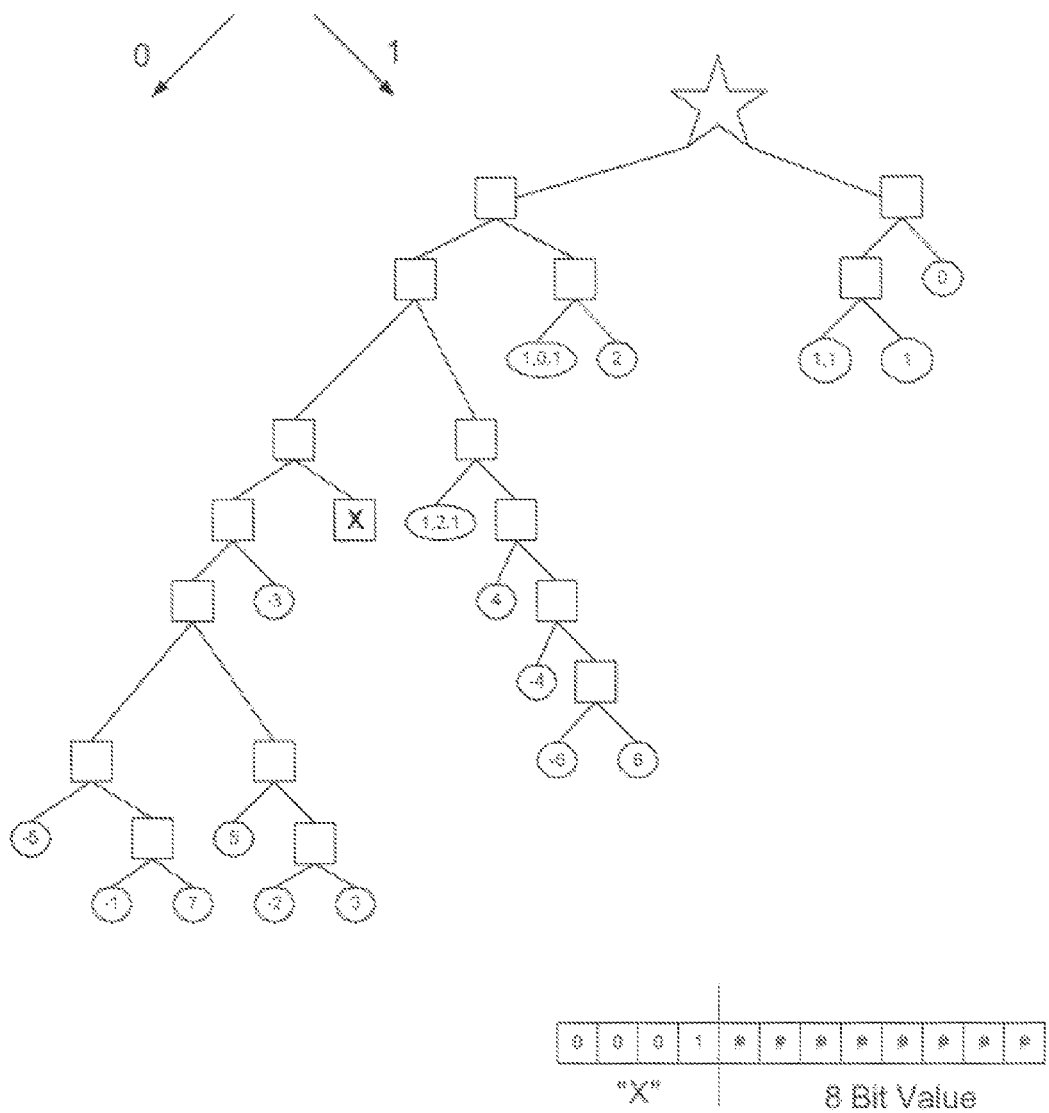
FIG. 14 is a schematic diagram illustrating a truncated encoding tree.

FIG. 14 is another example of a truncated entropy encoding tree. As previously addressed, the tree is a graphical representation of unambiguous codewords assigned to the highest probability values for a relevant waveform type. In the earlier example, unitary increments were assigned codewords from a value of −8 to 8, inclusive of 0 and also include the prefix codeword X. FIG. 14 illustrates that the code words are not limited to unitary values, but may in fact represent a string or sequence of 2 or more values. The most liking occurring unitary values or sequences are given the shortest codewords. Accordingly, the sequence of a "1" followed by another "1" is as probable as a single occurrence of a "1" and is more probable than a "4". In other words, if identifiable sequences have a high probability they may assigned codewords; which, with a limited set of available codewords will displace some other value.

The tree may be based upon generalized data. For example, over a wide patient population the sequence "1,0,1" might be quite common and hence incorporated into the tree stored in the memory of the encoder and decoder. Alternatively, the tree may be built upon collected data from a given source, such as a patient, shortly after implant. Finally, as noted above, the tree may be periodically updated through adaptive encoding. Thus, as data is actually collected and processed, repetitive sequences are detected and encoded. If, over time, this sequences changes, then the tree will continue to be updated as well.

The use of a codeword to represent a repetitive sequence of values will generally increase the compression ratio. A single 3 bit codeword is more efficient than four 3 bit codewords. However, not every repetitive sequence is efficiently replaced by a codeword. The efficiency gained by devoting a codeword to a sequence should be compared to the efficiency lost by either moving a unitary valued to a longer codeword (by either expanding the overall size of the tree or displacing another value) or removing that value from the tree entirely. As an example, if the sequence "0,0" occurred far more frequently than a single "0", then it may be more efficient to have the codeword for "0,0" equal to the binary value 11 and shift "0" to a longer codeword. Conversely, even if "0,0" occurs often but less than a single "0", then such a change would be less efficient. Also, if such a change were made, other values may shift as well. For example, a "1" may be moved to the illustrated value for "4" (assuming "1,0,1", "2", "1,2,1," and "X" would remain unchanged) on the tree; thus changing from a 3 bit value to a 5 bit value. Again, it would only be efficient to add the short codeword for "0,0" if the frequency of the "1" with a longer bit codeword permitted an overall increase in compression.

In summary, codewords may be utilized for unitary values or for sequences of two or more values that occur with sufficient frequency. While FIGS. 8 and 14 provide a means to illustrate the assigned values, it should be appreciated that the overall assignment of values occurs due to a probability distribution. The particular sequences considered will be evaluated in the same manner in such a probability distribution and assigned codewords accordingly.

The compression of sampled data with the present embodiments is lossless. That is, the reconstructed waveform will be identical to the sampled waveform after decoding. Often, the analysis of the collected waveforms requires a high degree of accuracy and lossy data compression (or loss due to other factors) could prevent accurate interpretation and the detection of significant events. On the other hand, noise and other extraneous variations in the collected waveform are also sampled and losslessly compressed.

The IMD 100 is provided, in some embodiments, with a smoothing module 160 (FIG. 1) to smooth or filter the data either prior to sampling or post-sampling. To the extent the particular application does not require precise waveform processing then known, generalized filtering techniques may be utilized. For example, a low pass filter may be provided to filter the analog data prior to sampling.

Figure 15:
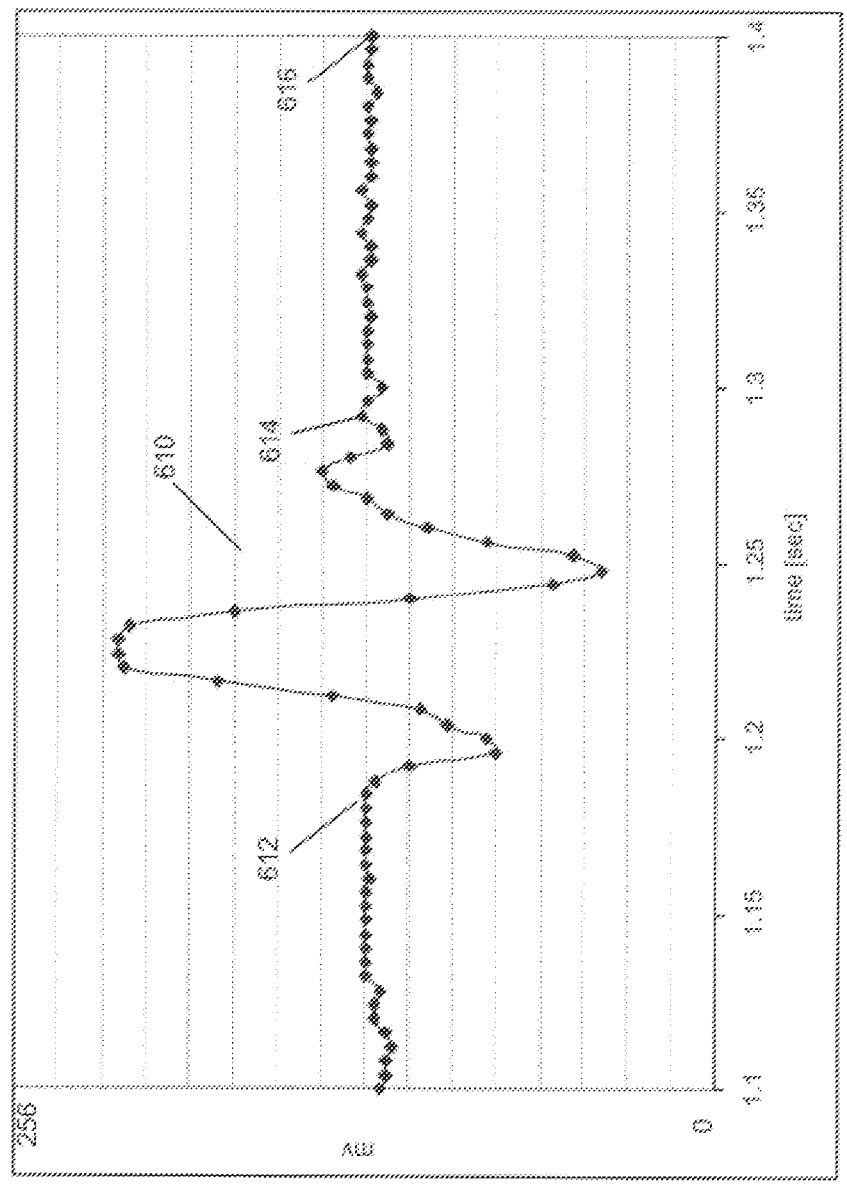
FIG. 15 is a sampled waveform.

FIG. 15 is a graph illustrating an exemplary waveform 600 with the linear analog signal in solid line and a plurality of sampled values indicated by diamonds. The X axis defines time (0.3 seconds) and the Y axis defines the signal value in milivolts or rather, the sample values assigned to the same.

The clinically significant portion of the illustrated waveform 600 is the QRS complex 610 that occurs approximately between data point 612 and data point 614. The overall width, shape, and amplitude of the QRS complex 610 may be important and if so, it would be undesirable to subject this portion of the waveform to a filtering function, such as a low pass filter. The data between data point 614 and the last illustrated data point 616 is relatively flat and the previously described encoding process would become even more effective if this portion of the data were smoothed. That is, the minor deflections noted are likely noise. The data points (614 to 616) could be replaced by zeroes. When parsed by the linear encoder, the value between the data points would be zero, which has the shortest available codeword. Further, if available, codewords for strings of zeros would also be available to increase compression. While there is a loss of some data, it is not significant to an analysis of the waveform 600.

While conceptually feasible, the selective application of filtering functions to portions of a waveform is challenging. That is, the IMD 100 would have to buffer data, analyze the waveforms, and selectively apply different filtering functions to different portions of the data. This is often not possible or practical with the time, memory and/or processing limitations of various implantable medical devices.

Thus, one embodiment consistent with the teachings of the present invention provides a digital smoothing function that will smooth relatively stable portions of a waveform but leave more dynamic portions generally unchanged. The smoothing function permits near real time data processing with minimal buffering requirements. The smoothing module 160 analyzes each data point and determines variability between that data point and those adjacent to it to determine a variance. If the variance exceeds a predetermined value, then the data point value utilized is set equal to the sampled data point. If the variance is below the predetermined value, then a formula is applied to adjust the value of the data point. For example, an average or a weighted average is obtained between the data point and those immediately adjacent to it and the average (or weighted average) value is then utilized as the sampled value. This will smooth functions where there is relatively minor variation from point to point; however, where larger changes are present, the smoothing function has no effect.

Figure 16:
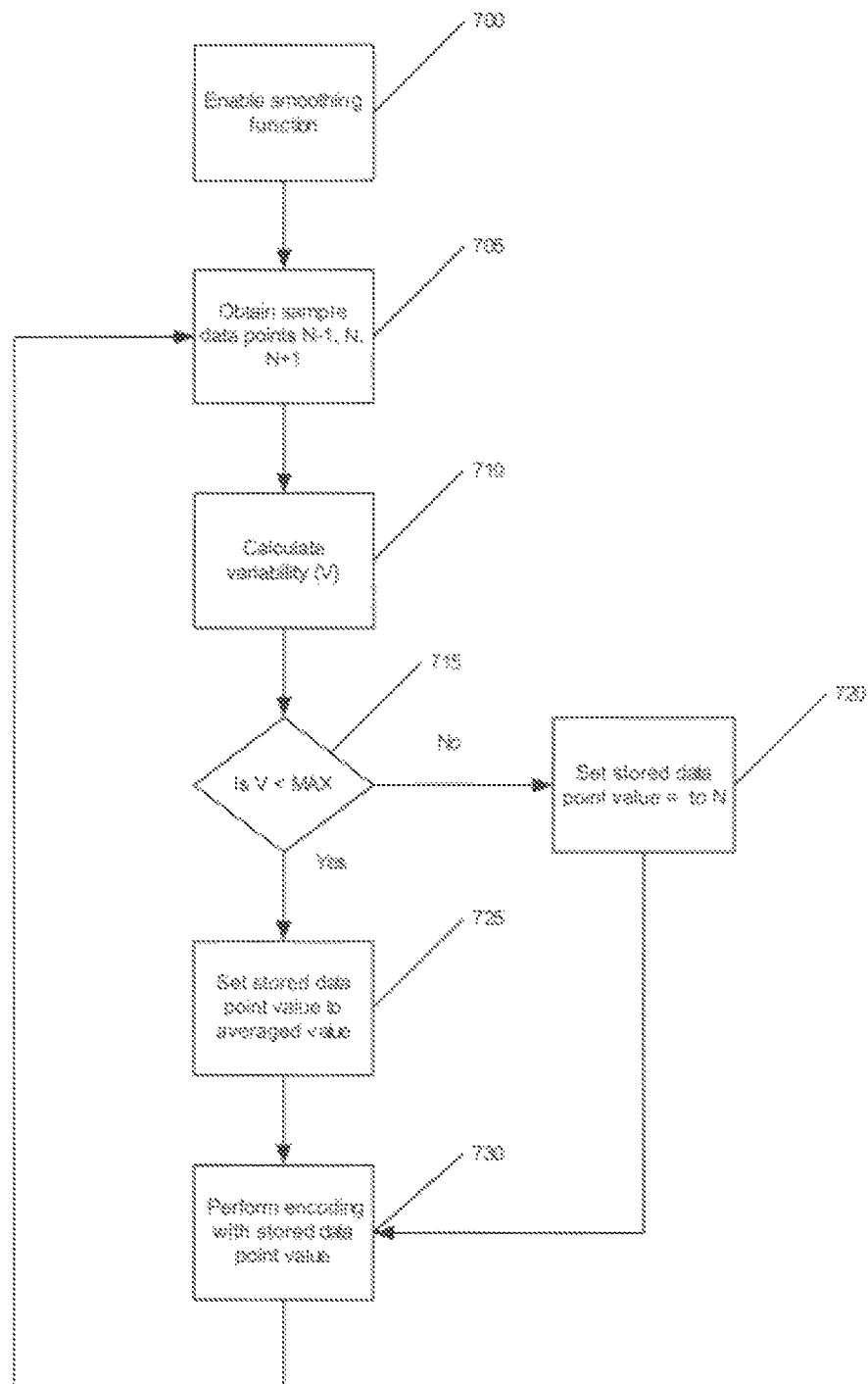
FIG. 16 is a flowchart of a smoothing process consistent with the teachings of the present invention.

FIG. 16 is a flowchart describing the smoothing algorithm. Initially, the IMD 100 enables (700) the smoothing function. Three sampled data points (N−1, N, N+1) are collected and compared (705). This set of data points is referred to as an adjustment set and will vary for each data point. More (or fewer) points could be utilized; however, the more points utilized the greater the impact of the smoothing function on more signification portions of the waveform. The comparison (705) of the three data points is performed to calculate (710) a value for variability between them.

For example, variability (V) may be calculated by:

$$V=|(N)-(N-1)|+|(N+1)-(N)|$$

The variability value (V) is then compared (715) to a predetermined maximum value (MAX). In one embodiment, MAX is equal to 5, but may be set to any value appropriate for the particular context. Thus, if any single point to point variation is equal to or greater than MAX or the absolute value of consecutive point to point variations sum to MAX or greater (e.g., 5), variability is deemed too high to apply the smoothing function to the current data point (N). As such, the sampled value for N is stored (720) in memory for data point $S_N$. During subsequent encoding (730), the value $S_N$ is used. The process then repeats for the next subsequent data point (e.g., N+1 is compared with N and (N+2)).

Assuming V<MAX, then the value $S_n$ is adjusted (725) and then stored. In one embodiment, $S_n$ is averaged over the adjustment set. For example, $$S_n=(N+(N-1)+(N+1))/3$$

In an alternative embodiment, $S_n$ is set to a weighted average. In some embodiments, the weighted average is raised (ceil (C++ functionality)) or lowered (floor (C++ functionality)) to the next integer value. For example, $$S_n=\text{floor}(\tfrac{1}{4}(N-1)+\tfrac{1}{2}(N)+\tfrac{1}{4}(N+1)); \text{ or}$$

$$S_n=\text{ceil}(\tfrac{1}{4}(N-1)+\tfrac{1}{2}(N)+\tfrac{1}{4}(N+1))$$

Regardless of whether one of these functions is specifically employed, the value is rounded to an integer value representative of the digital sampling interval. The value calculated is then stored in memory (or buffered) for the data point $S_N$. The process is repeated for the next data point N+1. In this manner, relatively stable portions of the waveform are smoothed while more dynamic portions are not; but this occurs on a point to point analysis so that the smoothing function itself is dynamically responsive.

The smoothing function is applied to the sampled data prior to using the linear predictive encoding. This leads to a smoother waveform from which the predictive values are encoded and hence, a shift too shorter codewords when entropy coding is applied. It should be appreciated that the smoothing function could be applied after the predictive encoding process. In addition, the signal could be smoothed both before and after the encoding process.

As previously presented, certain events may be used to initiate a period of time where entropy encoding is not utilized. For example, entropy encoding is disabled for a typical QRS duration upon sensing a ventricular depolarization. It should be appreciated that disabling entropy encoding may be utilized in combination with the smoothing function. In one embodiment, entropy encoding would be disabled for any data that does not pass through the smoothing filter. Alternatively, some predetermined number of higher variability data points must occur consecutively prior to disabling the entropy encoder either for those data points not parsed by the smoothing function or for a predetermined period of time.

While multiple embodiments have been disclosed, still other embodiments of the present invention will be apparent to those skilled in the art while remaining within the spirit and scope of the present invention. Accordingly, the drawings and detailed description are to be regarded as illustrative in nature and not restrictive. Numerous embodiments and examples have been described herein alone and in various combinations. It is contemplated that any and all of various embodiments and exampled may be combined in whole or in part whether or not specifically described herein and any such combination is considered within the spirit and scoped of the disclosure.

The invention claimed is:

1. An implantable medical device comprising:
    a sensor configured to sense a signal and to provide a digitally sampled signal; and
    a smoothing filter configured to process the sampled signal and classify a given data point of the sampled signal into a first type or a second type and to:
        apply a smoothing function to the given data point responsive to the given data point being classified as the first type, and
        to retain a sampled value for the given data point responsive to the given data point being classified as the second type,
    wherein the smoothing filter is configured to determine variability between the given data point and at least one sampled data point that is adjacent to the given data point, and
    classify the given data point into the first type if the variability is less than a predetermined variability value and into the second type if the variability is equal to or greater than the predetermined variability value.

2. The implantable medical device of claim 1, wherein the smoothing function applied to the first type of data is to determine an average value for the given data point and the data points adjacent to the given value.

3. The implantable medical device of claim 1, wherein the smoothing function applied to the first type of data is to determine a weighted average value for the given data point and the data points adjacent to the given value.

* * * * *